United States Patent
Kim et al.

(10) Patent No.: US 10,577,597 B2
(45) Date of Patent: Mar. 3, 2020

(54) NUCLEIC ACID EXTRACTION APPRATUS AND OPERATION METHOD THEREOF

(71) Applicant: NANOBIOSYS INC., Seoul (KR)

(72) Inventors: Sung Woo Kim, Seoul (KR); Jun Hur, Suwon-si (KR); Eun-Sub Kim, Bucheon-si (KR); Chi-Woo An, Bucheon-si (KR); Song Gyun Jung, Gwangmyeong-si (KR); Jae Young Byun, Anyang-si (KR); Duck Joong Kim, Anyang-si (KR); Mi Ree Kim, Ansan-si (KR); Do Hee Kim, Osan-si (KR); Kang Choi, Seoul (KR); Jin Pyung Kim, Seoul (KR)

(73) Assignee: NANOBIOSYS INC., Seoul (KR)

( * ) Notice: Subject to any disclaimer, the term of this patent is extended or adjusted under 35 U.S.C. 154(b) by 218 days.

(21) Appl. No.: 15/539,957

(22) PCT Filed: Dec. 22, 2015

(86) PCT No.: PCT/KR2015/014070
§ 371 (c)(1),
(2) Date: Jun. 26, 2017

(87) PCT Pub. No.: WO2016/105069
PCT Pub. Date: Jun. 30, 2016

(65) Prior Publication Data
US 2017/0342401 A1    Nov. 30, 2017

(30) Foreign Application Priority Data
Dec. 24, 2014 (KR) .................. 10-2014-0188192

(51) Int. Cl.
*C12N 15/10* (2006.01)
*B01L 3/00* (2006.01)
(Continued)

(52) U.S. Cl.
CPC .......... *C12N 15/1017* (2013.01); *B01L 3/502* (2013.01); *C12M 47/06* (2013.01);
(Continued)

(58) Field of Classification Search
None
See application file for complete search history.

(56) References Cited

U.S. PATENT DOCUMENTS

2002/0119576 A1* 8/2002 Sklar .................. B01L 3/50255
                                                            436/161
2008/0014610 A1    1/2008 Kamata et al.
(Continued)

FOREIGN PATENT DOCUMENTS

CN    102460107 A    5/2012
JP    08-035917 A    2/1996
(Continued)

*Primary Examiner* — Kathryn Wright
(74) *Attorney, Agent, or Firm* — Novick, Kim & Lee, PLLC; Sang Ho Lee

(57) ABSTRACT

In accordance with one embodiment of the present invention, there is disclosed an apparatus for nucleic acid extraction and an operation method thereof. The apparatus for nucleic acid extraction includes: a first rack having a plurality of sample tube receivers arranged in a circle; a second rack having a plurality of elution tube receivers arranged in a circle on an outer side thereof and a washing solution receiver positioned at the center thereof, a part of the washing solution receiver extending outwards to have projections formed in alternation with a plurality of the elution tube receivers; a main body having the first and second racks arranged to position the first rack on the top of the second rack; a rotational driver for separately rotating the first and second racks; a dispenser for separately dispensing a wash-
(Continued)

ing solution and an eluting solution into sample tubes; and a pressurizer for maintaining the inside of the sample tubes under raised pressure.

19 Claims, 16 Drawing Sheets

(51) Int. Cl.
*G01N 35/00* (2006.01)
*C12M 1/00* (2006.01)
*C12Q 1/68* (2018.01)
*C12Q 1/6806* (2018.01)
*G01N 35/04* (2006.01)
*G01N 35/02* (2006.01)
*G01N 35/10* (2006.01)

(52) U.S. Cl.
CPC ....... *C12N 15/1013* (2013.01); *C12Q 1/6806* (2013.01); *G01N 35/0098* (2013.01); *G01N 35/025* (2013.01); *G01N 2035/0455* (2013.01); *G01N 2035/1053* (2013.01)

(56) References Cited

U.S. PATENT DOCUMENTS

2011/0291004 A1* 12/2011 Kanda .................... G01N 1/405
250/288
2012/0079875 A1 4/2012 Nogami et al.

FOREIGN PATENT DOCUMENTS

JP 2006-223175 A 8/2006
KR 10-2004-0044981 A 5/2004
KR 10-0968477 B1 7/2010

* cited by examiner

NUCLEIC ACID EXTRACTION APPRATUS AND OPERATION METHOD THEREOF

TECHNICAL FIELD

The present invention relates to a nucleic acid extraction apparatus and an operation method thereof, and more particularly to a nucleic acid extraction apparatus and an operation method thereof to extract nucleic acids by a rotation-based drive.

The present invention is derived from the research supported by a grant of the Korea Health Technology R&D Project through the Korea Health Industry Development Institute (KHIDI), funded by the Ministry of Health & Welfare, Republic of Korea. (Grant No. HI13C2262, "Extensible Multiplex Real-time PCR of the health & medical technology research development project of the Korean Health Industry Development Institute (KHIDI) [Project No. HI13C2262; "Development of automated multiplex Real-time PCR assay system for lab chip-based simultaneous multichannel detection for ultrafast on-site diagnosis of malaria")

BACKGROUND ART

The polymerase chain reaction (PCR) for DNA amplification which is an essential step in biological research needs a large quantity of purified nucleic acids. This has led to limitations in the manual isolation of isolating biological substances or nucleic acids in university and corporate research labs. In order to overcome such limitations, automated apparatus for extracting biological substances or nucleic acids from biological specimens have been produced and used.

The conventional methods for nucleic acid extraction include a method of separating nucleic acids absorbed on a magnet using magnetic beads, a method of eluting a solution with a column to introduce air into the column and push the solution out, a method of eluting a solution through a centrifugal separation of the column, etc.

The automated equipment for nucleic acid extraction using the above-mentioned conventional methods is, however, problematic in terms of its relatively great bulkiness and excessively long processing time to process a large quantity of the specimens. Further, the specimens may cause contamination in the course of processing the specimens to reduce the processing efficiency and causing inconvenience to the user.

Accordingly, there is a demand for nucleic acid extraction apparatus and an operation method thereof that can solve these problems with the prior art.

DISCLOSURE OF INVENTION

To solve the problems with the prior art, it is an object of the present invention to provide an apparatus for nucleic acid extraction driven by rotation to easily extract nucleic acids from a sample solution and an operation method thereof.

The technical object of the present invention is not limited to the above-stated technical object, and other technical objects not mentioned above will be clearly understood by those skilled in the art according to the following descriptions.

In accordance with one embodiment of the present invention, an apparatus for nucleic acid extraction is provided that includes: a first rack having a plurality of sample tube receivers arranged in a circle; a second rack having a plurality of elution tube receivers arranged in a circle on an outer side thereof and a washing solution receiver positioned at the center thereof, a part of the washing solution receiver extending outwards to have projections formed in alternation with a plurality of the elution tube receivers; a main body having the first and second racks arranged to position the first rack on the top of the second rack; a rotational driver for separately rotating the first and second racks; a dispenser for separately dispensing a washing solution and an eluting solution into sample tubes; and a pressurizer for maintaining the inside of the sample tubes under raised pressure.

Preferably, at least either one of the first rack or the second rack is horizontally movable with respect to the main body.

Preferably, at least either one of the first rack or the second rack is detachable from the main body.

Preferably, the nucleic acid extraction apparatus may further include a washing solution collector formed in the bottom of the second rack and connected to the washing solution receiver to allow fluid communication.

Preferably, the nucleic acid extraction apparatus may further include a plurality of sample tubes comprising a filter member for absorbing nucleic acid molecules and a fixing portion for fixing the filter member to the inside thereof, and being placed into the sample tube receivers of the first rack; and a plurality of elution tubes being received in the elution tube receivers of the second rack.

Preferably, the nucleic acid extraction apparatus may further include at least one washing solution container for storing the washing solution; and at least one eluting solution container for storing the eluting solution.

Preferably, the rotational driver drives the first and second racks to have an arrangement rotation so that the sample tubes of the first rack are positioned on the washing solution receiver or the elution tubes of the second rack.

Preferably, the dispenser injects the washing solution into the sample tubes when the rotational driver drives the first and second racks to have a synchronous rotation after an arrangement rotation for positioning the sample tubes of the first rack on the washing solution receiver of the second rack.

Preferably, the dispenser injects the eluting solution into the sample tubes when the rotational driver drives the first and second racks to have a synchronous rotation after an arrangement rotation for positioning the sample tubes of the first rack on the elution tubes of the second rack.

In accordance with another embodiment of the present invention, an operation method for a nucleic acid extraction apparatus is provided that includes: driving first and second racks to have an arrangement rotation and position a sample tube received into the first rack on a washing solution receiver of the second rack, wherein the sample tube receives a sample solution containing nucleic acids and impurities, the nucleic acids being absorbed onto a filter member in the sample tube; performing a washing operation while driving the first and second racks to have a synchronous rotation; driving the first and second racks to have an arrangement rotation and position the sample tube received into the first rack on an elution tube of the second rack; and performing an eluting operation while driving the first and second racks to have a synchronous rotation.

Preferably, the washing operation step is performed by driving a synchronous rotation of the first and second racks to inject a washing solution into the sample tube and maintain the inside of the sample tube under raised pressure, wherein the washing solution is used to release the impurities from the filter member rather than the nucleic acids absorbed onto the filter member.

In addition, preferably, the eluting operation step is performed by driving a synchronous rotation of the first and second racks to inject an eluting solution into the sample tube and maintain the inside of the sample tube under raised pressure, wherein the eluting solution is used to release the nucleic acids absorbed onto the filter member into the elution tube.

In addition, preferably, at least either one of the washing operation step or the eluting operation step may be repeatedly performed.

Effects of the Invention

According to the present invention, by driving individual racks in a rotating manner, it is possible to simplify the motion configuration involved in nucleic acid extraction, enhance the processing speed, reduce the production cost, and enable a design for a compact product.

According to the present invention, the racks are driven to have an arrangement rotation and a synchronous rotation, making it possible to eliminate cross-contamination or interference of the respective elution tube receivers with the eluting solution and/or the washing solution.

Further, according to the present invention, since the individual racks are coupled to the main body so as to be horizontally movable, it offers convenience to the user, such as making it easier to maintain the racks and to receive and detach the sample tubes and elution tubes.

In addition, according to the present invention, the nucleic acid extracts are received in the elution tubes, thereby eliminating the inconvenience of performing separate pipetting for storage of the nucleic acids.

BRIEF DESCRIPTIONS OF DRAWINGS

A brief description will be given as to the individual drawings for the sake of better understanding of the drawings mentioned in the detailed description of the present invention.

BEST MODES FOR CARRYING OUT THE INVENTION

Figure 1A:
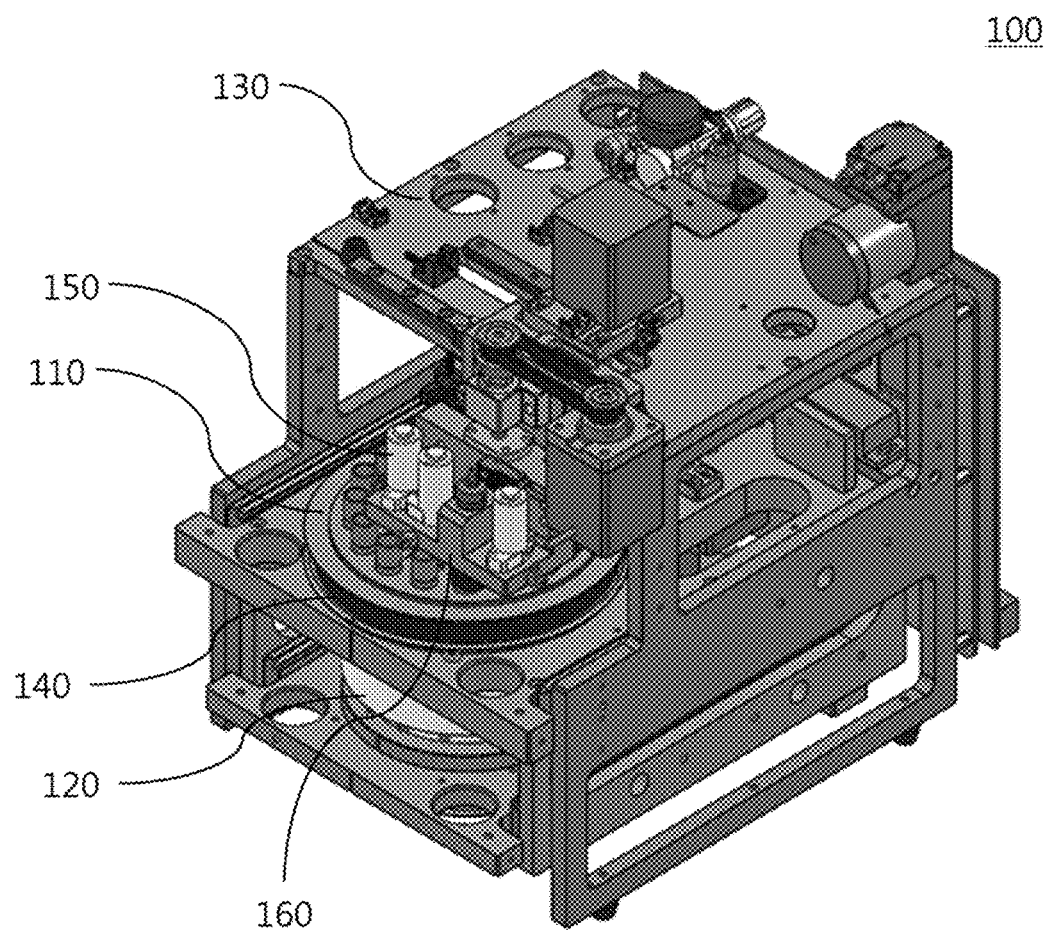
FIGS. 1a and 1b are illustrations of an apparatus for nucleic acid extraction in accordance with one embodiment of the present invention.

Hereinafter, the embodiments of the present invention will be described in further detail with reference to the accompanying drawings. In designating reference numerals to the components of the drawings, the same reference numerals are used throughout the different drawings to designate the same or similar components. In the description of the present invention, a detailed description of known functions and configurations incorporated herein will be omitted when it may make the subject matter of the present invention rather unclear. While the invention will be described in connection with preferred embodiments, it will be understood that the technical conceptions of the present invention are not confined or limited to the embodiments but implemented by those skilled in the art to cover various modifications.

Throughout the specification, when an element is referred to as being "connected" or "coupled" to another element, it can be "directly connected or coupled" to the other element or "indirectly connected or coupled" to the other element while intervening elements may be present. In this specification, the terms "comprises" and/or "comprising" or "includes" and/or "including" specify the presence of stated elements and/or components. but unless stated otherwise, they do not preclude the presence or addition of one or more other elements and/or components. Moreover, the terms "first", "second", "A", "B", (a), (b), etc. may be used in the description of the elements in the embodiment of the present invention. These terms are only used to distinguish one element from another and not given to confine the substance, sequence, order, or the like of the element.

Figure 1B:
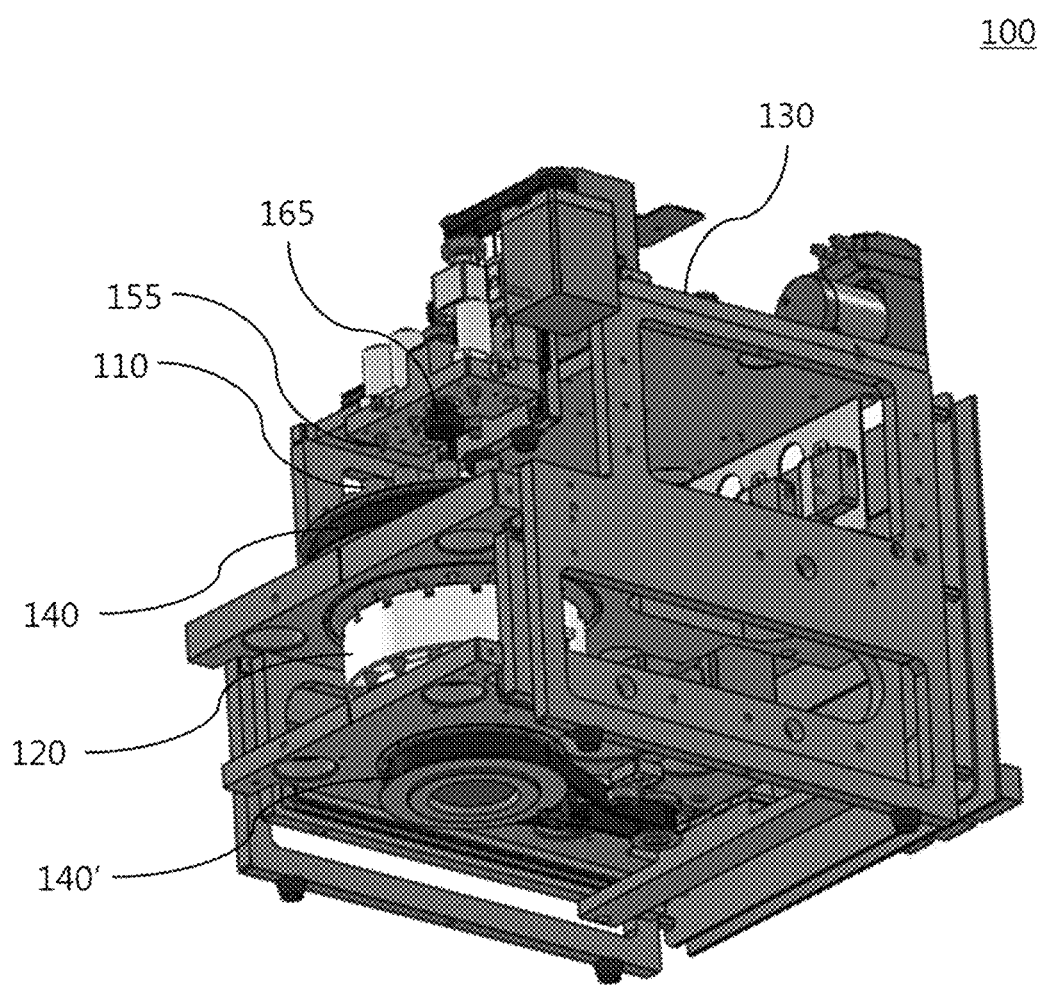
Figure 2A:
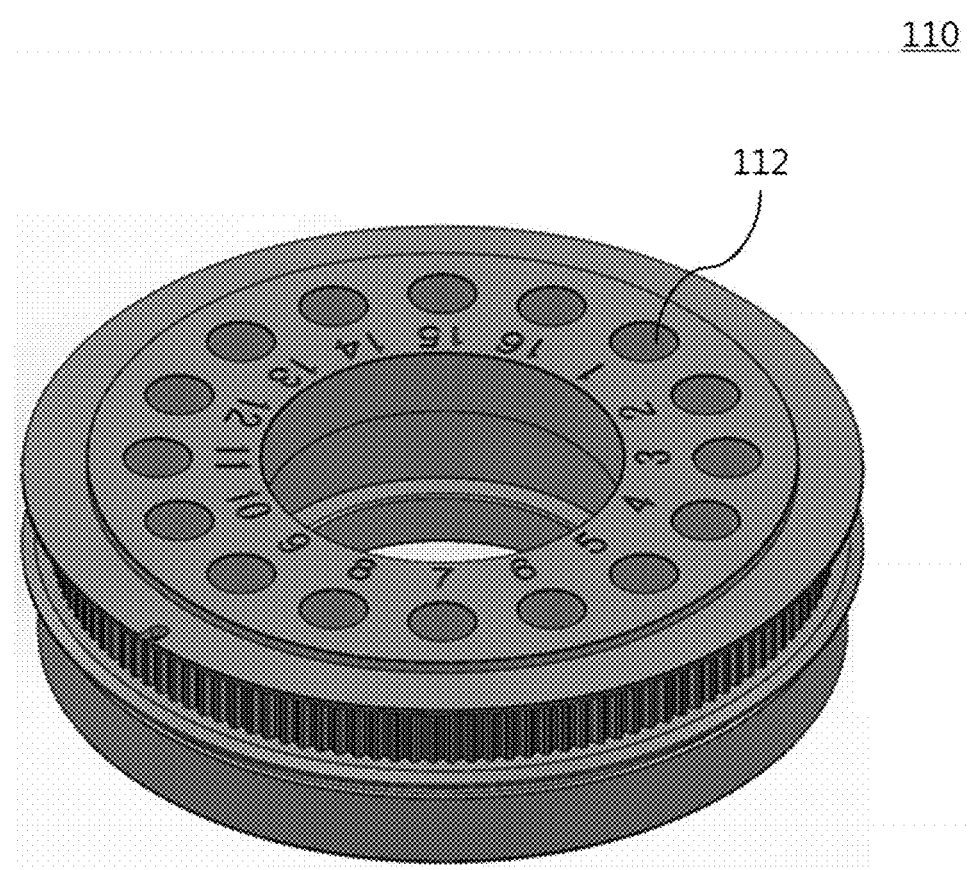
FIGS. 2a to 2c are illustrations of a first rack of the apparatus for nucleic acid extraction in accordance with one embodiment of the present invention.
Figure 2B:
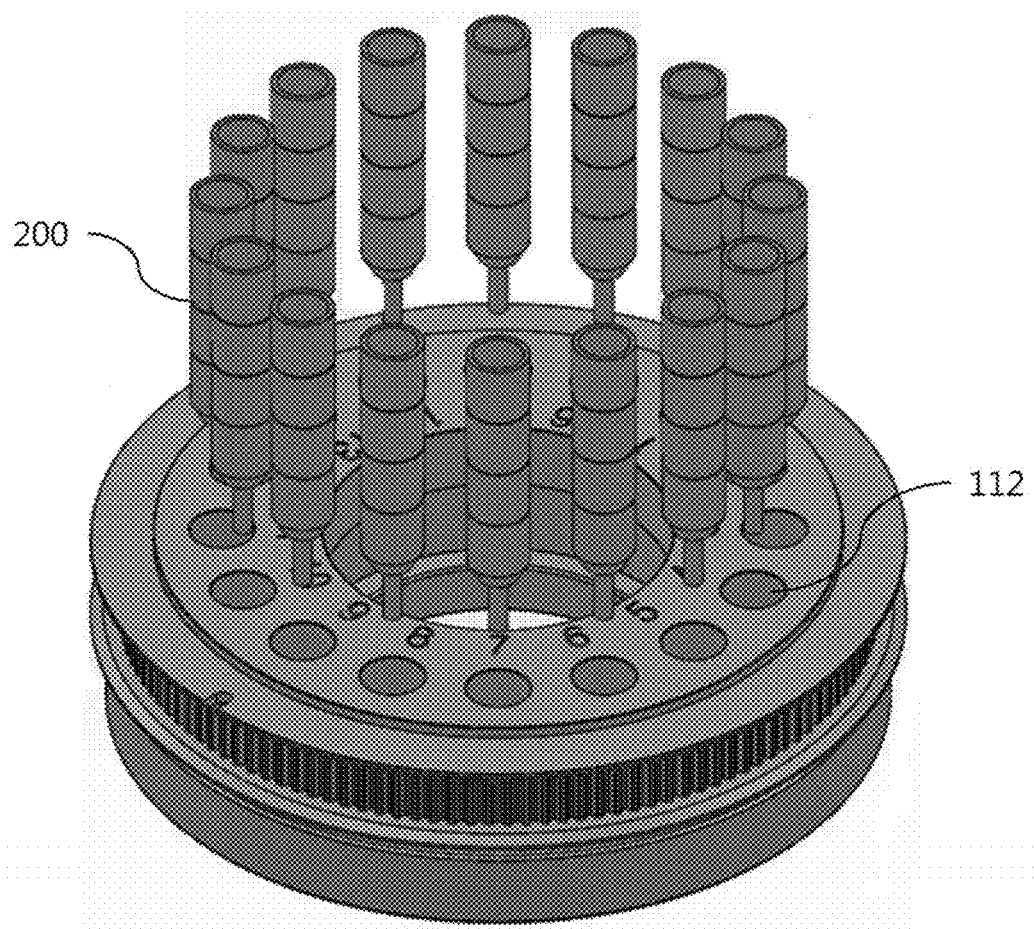
Figure 2C:
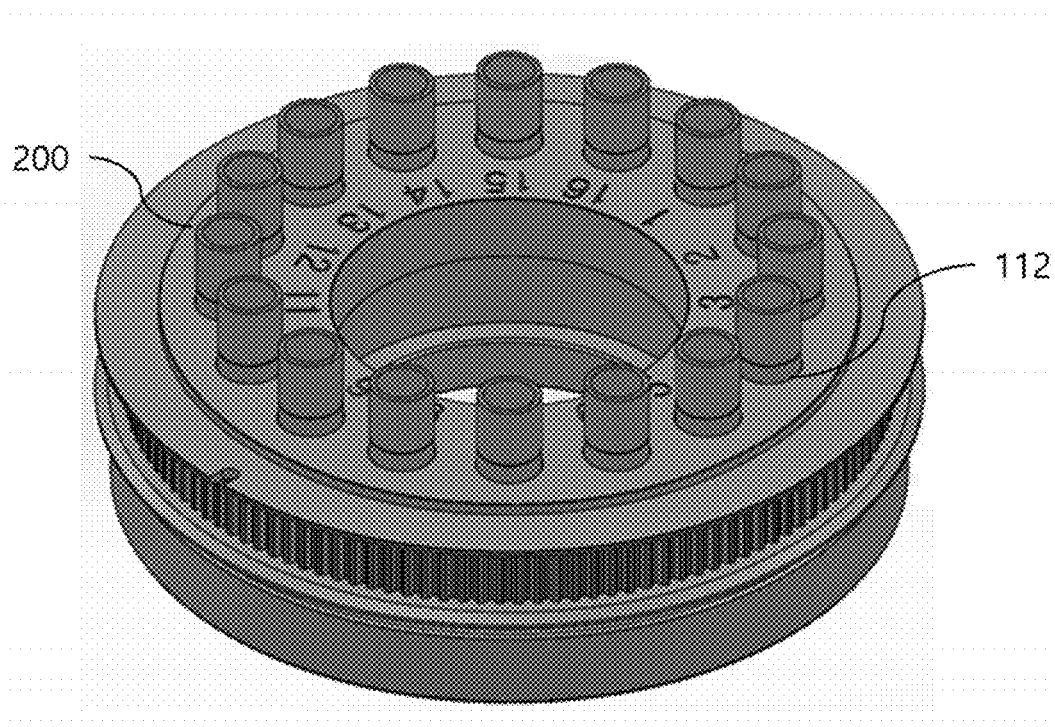
Figure 3A:
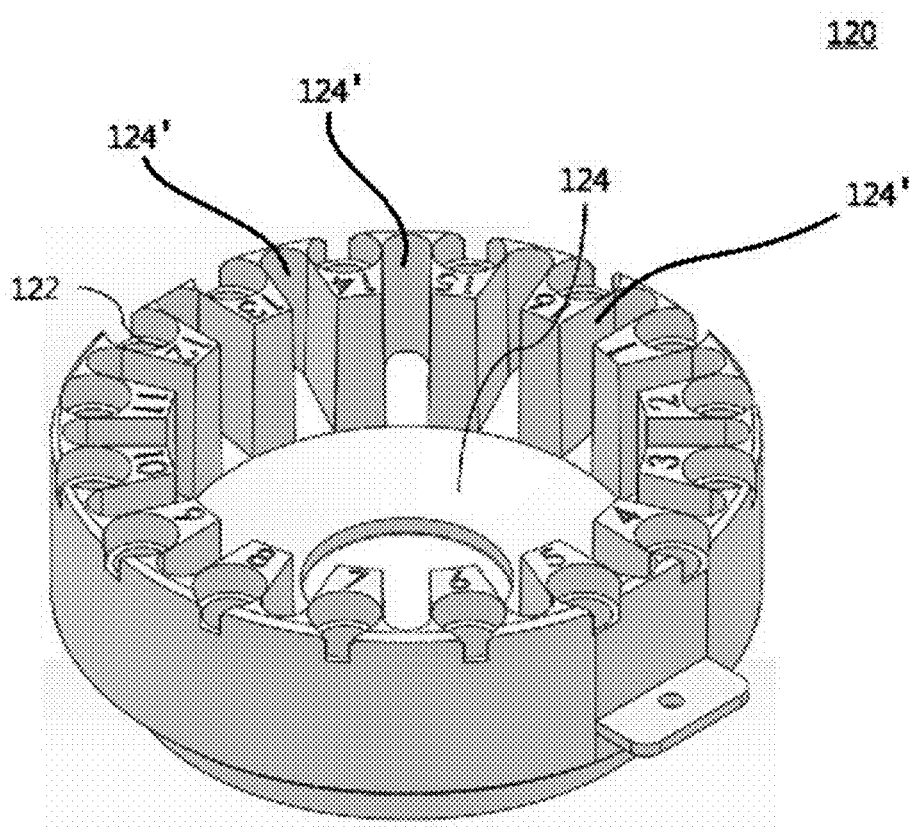
FIGS. 3a to 3c are illustrations of a second rack of the apparatus for nucleic acid extraction in accordance with one embodiment of the present invention.
Figure 3B:
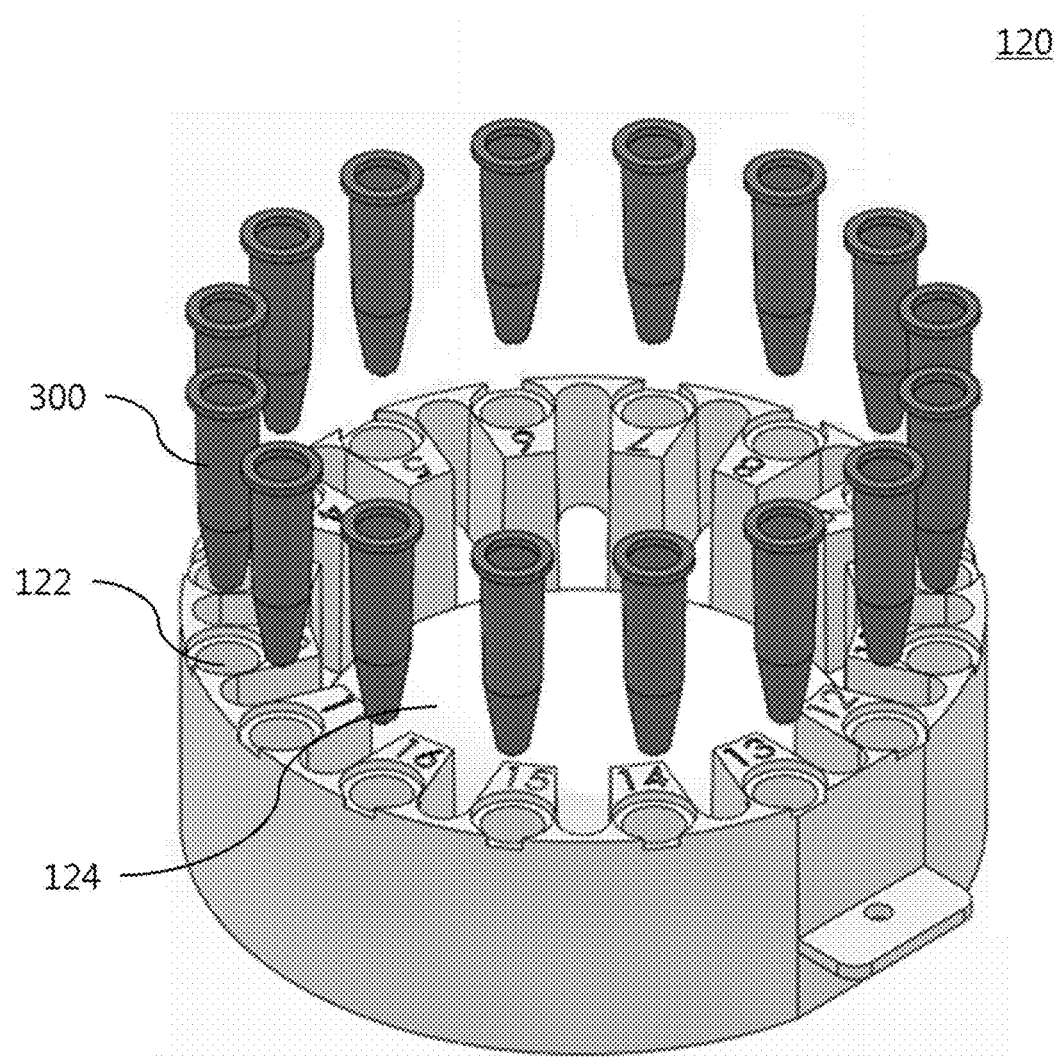
Figure 3C:
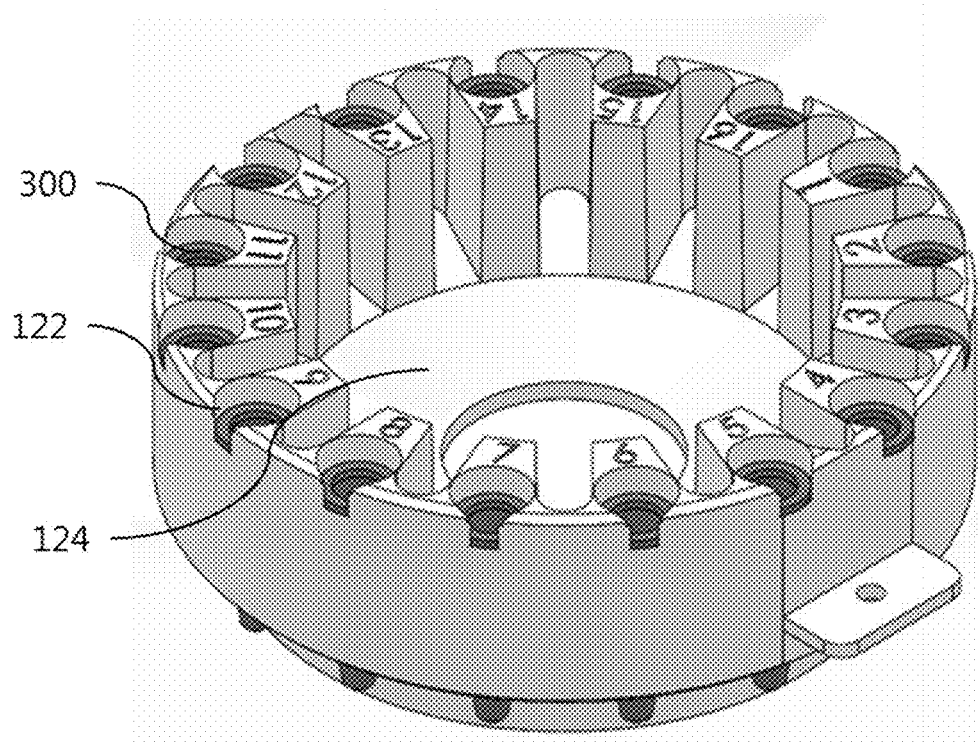

FIGS. 1a and 1b are illustrations of an apparatus for nucleic acid extraction in accordance with one embodiment of the present invention. FIGS. 2a to 2c are illustrations of a first rack of the apparatus for nucleic acid extraction in accordance with one embodiment of the present invention. FIGS. 3a to 3c are illustrations of a second rack of the apparatus for nucleic acid extraction in accordance with one embodiment of the present invention.

As illustrated, an apparatus 100 for nucleic acid extraction may have a first rack 110, a second rack 120, a main body 130, rotational drivers 140 and 140', a dispenser 150, and a pressurizer 160.

The first rack 110 is for receiving and fixing sample tubes 200. For its purpose, the first rack 110 may have a plurality of sample tube receivers 112 for receiving sample tubes 200. A plurality of the sample tube receivers 112 are positioned apart from one another and arranged in a circle. Each sample tube receiver 112 is designed to receive each sample tube 200 and may have an opening in the bottom to transfer an extracted solution from the sample tube downwards. The sample tube receivers 112 are not only positioned apart from one another to prevent contamination or interference of the sample tubes 200, but also arranged in a circle, as will be described below in further detail, to perform an operation of arrangement for nucleic acid extraction just by the rotation of the rotational drivers 140 and 140'.

The second rack 120 is for receiving and fixing elution tubes 300 and receiving a washing solution. For its purpose, the second rack 120 may include elution tube receivers 122 and a washing solution receiver 124.

The elution tube receivers 122 are to receive and fix the elution tubes 300. A plurality of the elution tube receivers 122 may be positioned apart from one another and arranged in a circle along the circumference of the second rack 120. The elution tube receivers 122 are positioned apart from one another, so it is possible to prevent contamination or interference of the elution tube receivers 122 by the extracted substance from the sample tubes 200. In addition, as will be described below in further detail, the elution tube receivers 122 is designed to perform an operation of arrangement for nucleic acid extraction just by the rotation of the rotational drivers 140 and 140'. The elution tubes 300 received and fixed into the elution tube receivers 122 are for receiving the extracted nucleic acids from the first rack 110, so they can individually receive the extracted nucleic acids from the respective sample tubes 200. This makes it possible to eliminate the need of transferring the extracted nucleic acids through a separate pipette.

The washing solution receiver 124, which is for receiving a washing solution, is positioned at the center of the second rack 120. At least a portion of the washing solution receiver 124 may be extended outwardly to have a plurality of projections 124', which are formed in alternation with a plurality of the elution tube receivers 122. As the washing solution receiver 124 has the extended portion formed in alternation with a plurality of the elution tube receivers 122, it is enabled to perform an operation of arrangement for reception of the washing solution simply by the rotation of the rotational driver 140.

The main body 130 is a frame of the apparatus 100 for nucleic acid extraction. The first rack 110, the second rack 120, the rotational driver 140, the dispenser 150, and the pressurizer 160 may be disposed at the main body 130. Particularly, on the main body 130, the first rack 110 may be positioned on the top of the second rack 120. This makes it possible to collect the extracts (e.g., nucleic acids, etc.) from the sample tubes 200 of the first rack 110 right onto the second rack 120.

The rotational drivers 140 and 140' are connected to the first and second racks 110 and 120 to rotate the first and second racks 110 and 120, respectively. The rotation by the rotational drivers 140 and 140' may include an arrangement rotation or a synchronous rotation of the first and second racks 110 and 120. The arrangement rotation may include rotating the first and second racks 110 and 120 to arrange so that the sample tubes 200 received into the first rack 110 are lined up with the washing solution receiver 124 or the elution tubes 300 of the second rack 120. Such an arrangement is to use different receivers for the extracts in reply to the use of a washing solution or an eluting solution. The synchronous rotation means synchronously rotating the first and second racks 110 and 120 which are arranged by the arrangement rotation. As the synchronous rotation causes the first and second racks 110 and 120 to rotate in a synchronous manner, the relative positions of the sample tubes 200 and the washing solution receiver, or the relative positions of the sample tubes 200 and the elution tubes 300 can be maintained all the same. As will be described below in further detail, the washing solution or the eluting solution may be injected into the sample tubes 200 in the first rack 110 at the same time of the synchronous rotation.

The dispenser 150 may inject a predetermined fluid into the sample tubes 200 through a dispensing nozzle 155. The fluid, used for nucleic acid extraction, may include a washing solution, an eluting solution, etc. In accordance with one embodiment of the present invention, the dispenser 150 may include different dispensing nozzles 155 by the fluids in order to avoid a risk of cross-contamination of the different fluids. In one embodiment, the dispenser 150 may include a plurality of dispensing nozzles capable of performing a simultaneous operation for a plurality of the sample tubes 200 to improve the rate of nucleic acid extraction.

The pressurizer 160 is designed to pressurize the sample tubes 200. For this purpose, the pressurizer 160 may include a pressurizing nozzle 165 for injecting a pressurized air into the sample tubes 200. The injection of the pressurized air into the sample tubes 200 maintains the inside of the sample tubes 200 under the raised pressure to make at least a part of the fluid of the sample tubes 200 to pass through a filter member in the sample tubes 200 and to be extracted onto the second rack 120. In one embodiment, the pressurizer 160 may include a plurality of pressurizing nozzles 165 capable of performing a simultaneous operation for a plurality of the sample tubes 200 to improve the rate of nucleic acid extraction.

In accordance with one embodiment of the present invention, at least either one of the first rack 110 or the second rack 120 may be detachably attached to the main body 130. Namely, at least one of the first rack 110 or the second rack 120 is constructed to be detachable from the main body 130. It is possible to facilitate the use and maintenance of the racks, including installation or detachment of different tubes, discharge of the washing solution, etc.

The shape or structure of the apparatus 100 for nucleic acid extraction as illustrated in FIGS. 1, 2 and 3 is given as an example and may vary according to the adopted embodiment of the present invention.

Figure 4:
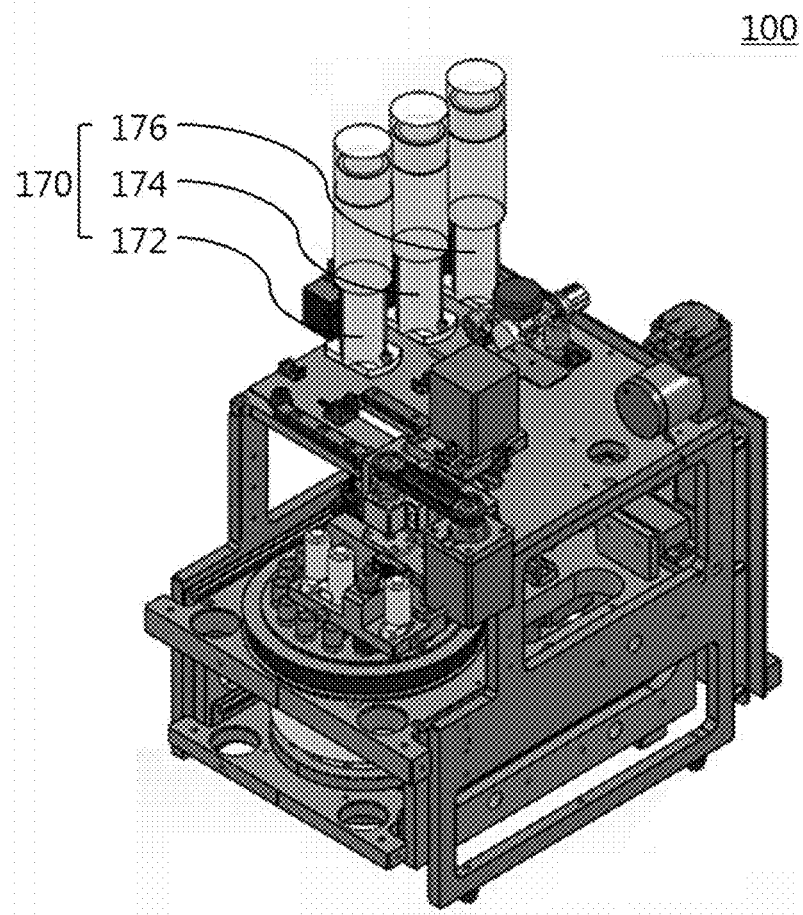
FIG. 4 is an illustration of an apparatus for nucleic acid extraction in accordance with one embodiment of the present invention.

FIG. 4 is an illustration of an apparatus for nucleic acid extraction in accordance with one embodiment of the present invention.

As illustrated, the apparatus 100 for nucleic acid extraction may include a plurality of containers 170.

A plurality of the containers 170 may include at least one washing solution container 172 and 174 for storing a washing solution, and at least one eluting solution container 176 for storing an eluting solution. Each container 170 is connected to the dispenser 150, which may dispense the solution stored in each container 170 into the sample tubes 200.

FIG. 4 shows two washing solution containers 172 and 174 and one eluting solution container 176, the number of the containers 170 and the type of the stored fluids may vary according to the embodiment of the present invention.

Figure 5:
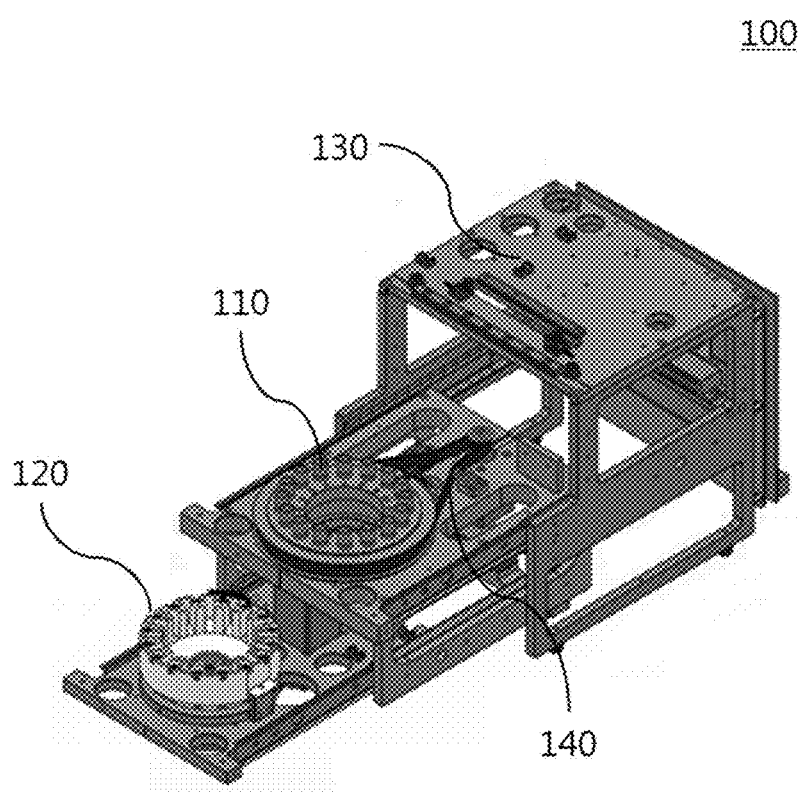
FIG. 5 is an illustration of an apparatus for nucleic acid extraction in accordance with one embodiment of the present invention.

FIG. 5 is an illustration of an apparatus for nucleic acid extraction in accordance with one embodiment of the present invention.

As shown in FIG. 5, the first and second racks 110 and 120 may be separately movable in a horizontal direction with respect to the main body 130. The horizontal movement of the first and second racks 110 and 120 with respect to the main body 130 may be implemented to have direct or indirect horizontal movement to the main body 130. As the first and second racks 110 and 120 are enabled to move in a horizontal direction, it is easier not only to maintain the first and second racks 110 and 120, but also to receive or remove the sample tubes 200, the elution tubes 300, and the first and second racks 110 and 120 for nucleic acid extraction.

FIG. 5 shows the first rack 110 capable of making a direct horizontal movement to the main body 130 and the second rack 120 capable of making an indirect horizontal movement to the main body 130 (that is, a direct movement to the first rack 110), various configurations other than this one may be applied according to the adopted embodiment of the present invention. In addition, a part of the components of the apparatus 100 for nucleic acid extraction are not shown in FIG. 5 to make the illustration simple, but they are not to be excluded in the embodiment of the present invention.

Figure 6:
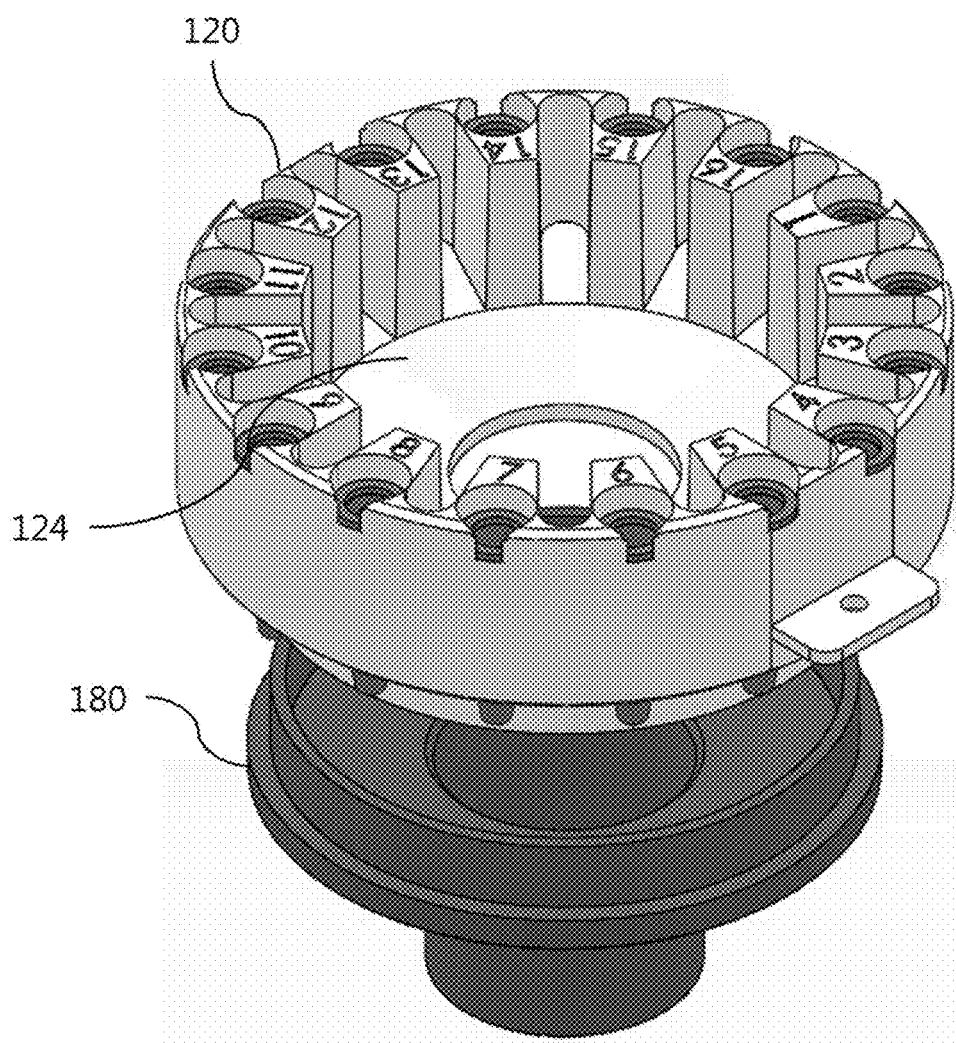
FIG. 6 is an illustration of an apparatus for nucleic acid extraction in accordance with one embodiment of the present invention.

FIG. 6 is an illustration of an apparatus for nucleic acid extraction in accordance with one embodiment of the present invention.

As illustrated, the apparatus 100 for nucleic acid extraction may further include a washing solution collector 180. The washing solution collector 180, which is to collect a washing solution received in the washing solution receiver 124 in the second rack 120, may be connected to the one end of the washing solution receiver 124 of the second rack 120 to allow a fluid communication with the washing solution receiver 124.

More specifically, the washing solution receiver 124 in the second rack 120 may have an opening in its one region so that the washing solution received in the washing solution receiver 124 can be discharged through the opening. The washing solution collector 180 may be positioned at the bottom of the second rack 120 to collect a washing solution discharged through the opening of the washing solution receiver 124. The washing solution collector 180 is detachably attached to the second rack 120, so its removal makes it easier to maintain the apparatus 100 for nucleic acid extraction, including collection and discharge of the washing solution or the like.

The shape of the washing solution collector 180 illustrated in FIG. 6 is provided for exemplary purpose only and may vary according to the adopted embodiment of the present invention.

Figure 7:
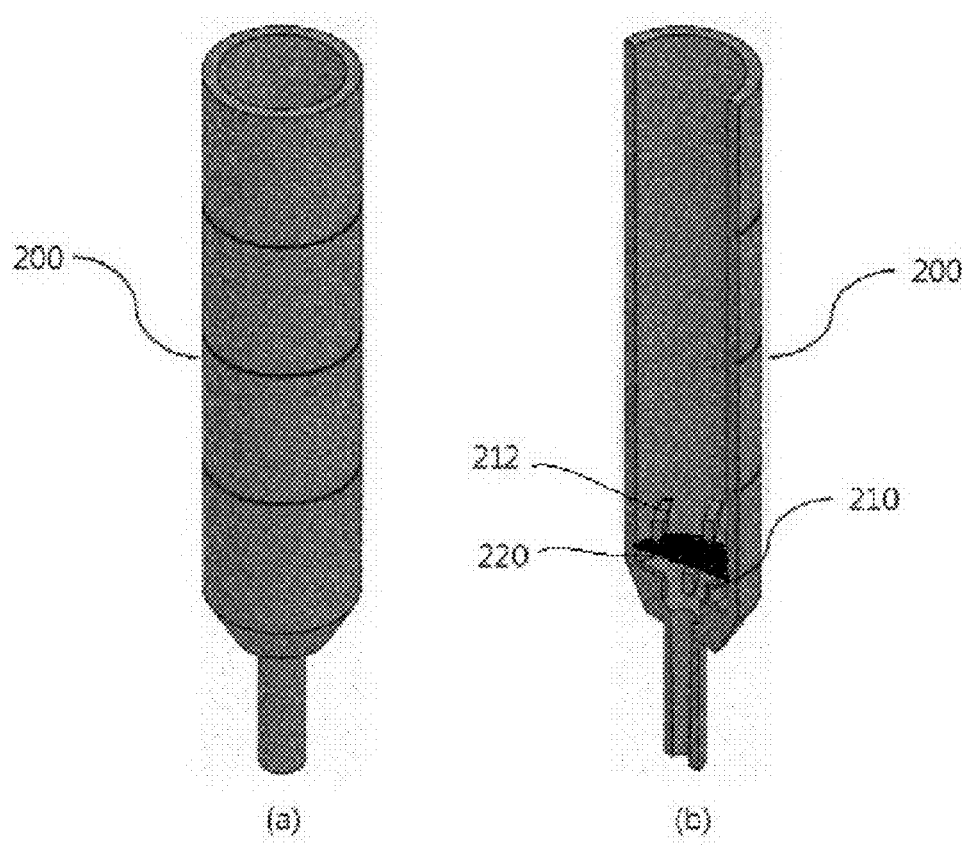
FIG. 7 is an illustration of a sample tube in accordance with one embodiment of the present invention.

FIG. 7 is an illustration of a sample tube in accordance with one embodiment of the present invention.

The sample tube 200 is to receive a sample solution containing nucleic acids and impurities. Both ends of the sample tube 200 may have an opening, as shown in FIG. 5. Particularly, the bottom opening may be narrower than the top opening. This secures a stable transfer of the extracted substances from the sample tube 200 to the elution tubes 300 or the washing solution receiver 124 in the second rack 120.

In addition, the sample tube 200 may include a filter support 210. The filter support 210 is a projection of a fabric having a tapered cross-sectional area as disposed in one inside region of the sample tube 200, particularly formed inwards in the region. A filter member (not shown) may be placed on the projecting filter support 210. The filter member is to absorb nucleic acids and may include, for example, porous membranes, etc. In addition to the filter member, a filter fixer 212 may be further placed on the filter member. The filter fixer can fix the position and placement of the filter member from the top of the filter member.

In this manner, the filter support 210 and the filter fixer are used to support and fix the filter member from the top and bottom of the filter member at the same time, thereby preventing the performance reduction of the filter caused when the filter is movable rather than fixed.

The shape or structure of the sample tube 200 shown in FIG. 7 in given for exemplary purpose only and may vary according to the adopted embodiment of the present invention.

Figure 8:
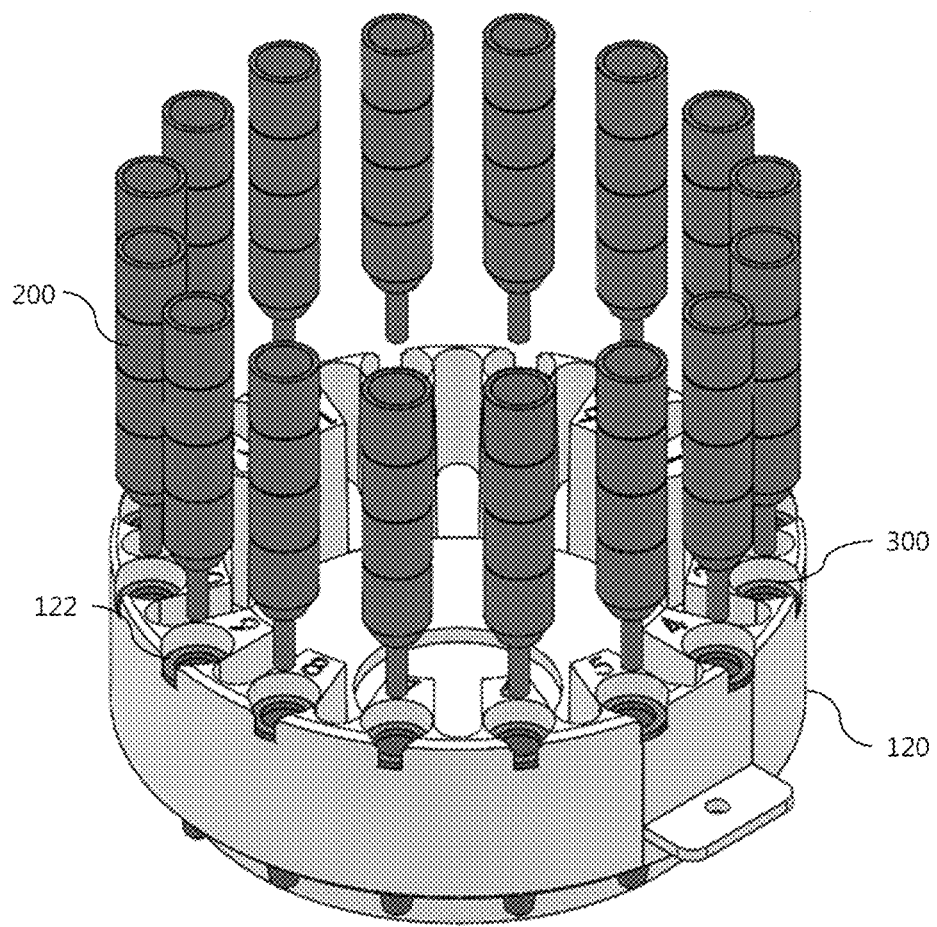
FIG. 8 shows an operational example of the apparatus for nucleic acid extraction in accordance with one embodiment of the present invention.

FIG. 8 shows an operational example of the apparatus for nucleic acid extraction in accordance with one embodiment of the present invention.

As illustrated, the rotational drivers 140 and 140' drive the first and second racks 110 and 120 to have an arrangement rotation so that the sample tubes 200 of the first rack 110 are lined up to be positioned corresponding to the washing solution receiver 124 in the second rack 120. Then, the rotational drivers 140 and 140' drive the first and second racks 110 and 120 to have a synchronous rotation so that the relative positions of the sample tubes 200 in the first rack 110 and the washing solution receiver 124 in the second rack 120 are maintained all the same. At the same time of the synchronous rotation, the dispenser 150 injects a washing solution into the sample tubes 200 and the pressurizer 160 maintains the inside of the sample tubes 200 under raised pressure. In this manner, a washing operation can be carried out sequentially on the respective sample tubes 200 arranged on the first rack 110.

In other words, the present invention can continuously perform injection of the washing solution into a plurality of samples and pressurization of the sample through the synchronous rotation following the arrangement rotation.

Figure 9:
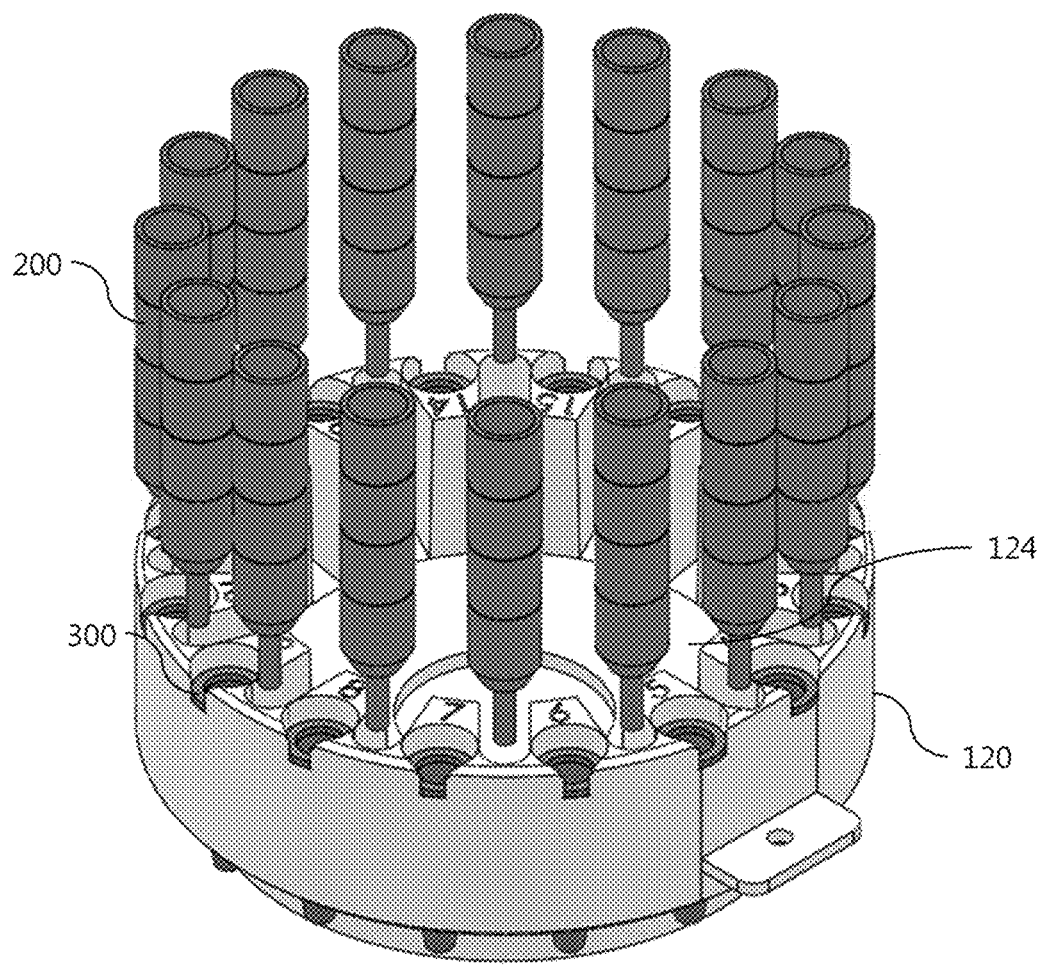
FIG. 9 shows an operational example of the apparatus for nucleic acid extraction in accordance with one embodiment of the present invention.

FIG. 9 shows an operational example of the apparatus for nucleic acid extraction in accordance with one embodiment of the present invention.

As illustrated, the rotational driver 140 may drive the first and second racks 110 and 120 to have an arrangement rotation so that the sample tubes 200 of the first rack 110 are positioned on the elution tubes 300 of the second rack 120. Then, the rotational driver drives the first and second racks 110 and 120 to have a synchronous rotation so that the relative positions of the sample tubes 200 of the first rack 110 and the elution tubes 300 of the second rack 120 are maintained all the same. At the same time of the synchronous rotation, the dispenser 150 injects an eluting solution into the sample tubes 200 and the pressurizer 160 maintains the inside of the sample tubes 200 under raised pressure. In this manner, an eluting operation can be performed sequentially on the respective sample tubes 200 arranged on the first rack 110.

In other words, the present invention can continuously perform injection of the eluting solution into a plurality of samples and pressurization of the sample through the synchronous rotation following the arrangement rotation.

Figure 10:
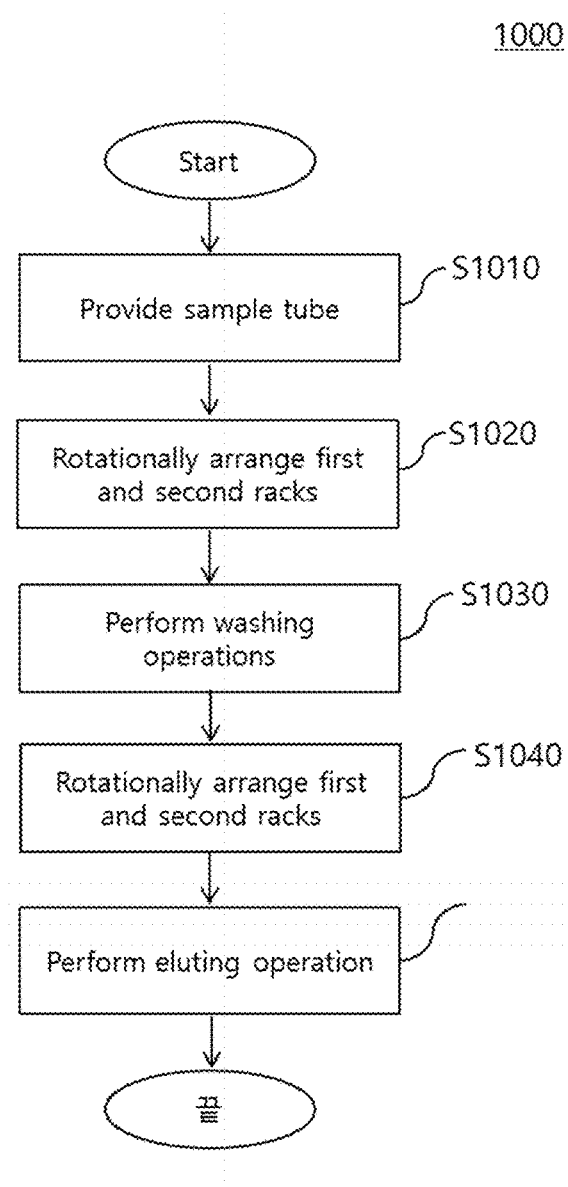
FIG. 10 shows an operation method for the apparatus for nucleic acid extraction in accordance with one embodiment of the present invention.

FIG. 10 shows an operation method for the apparatus 100 for nucleic acid extraction in accordance with one embodiment of the present invention.

Firstly, sample tubes 200 receiving a sample solution are provided, in step S1010. The step S1010 may be performed by having the sample tubes 200 received into the sample tube receiver 112 of the first rack 110. In this regard, the sample solution contains nucleic acids and impurities, and the nucleic acids are absorbed onto the filter member in each sample tube 200.

Subsequently, the first and second racks 110 and 120 are driven to have an arrangement rotation, in step S1020. The step S1020 is to arrange the positions of the first and second racks 110 and 120 in order to perform a washing operation with the sample solution. More specifically, the rotational drivers 140 and 140' rotate at least either one of the first rack 110 or the second rack 120 so that the sample tubes 200 received into the first rack 110 are positioned on the washing solution receiver 124 of the second rack 120 (Refer to FIG. 8).

Subsequently, a washing operation is carried out when the first and second racks 110 and 120 are driven to have a synchronous rotation, in step S1030. The step S1030 is performed in such a manner that the rotational drivers 140 and 140' drive the first and second racks 110 and 120 to have a synchronous rotation, so the dispenser 150 injects a washing solution into the sample tubes 200 and the pressurizer 160 maintains the inside of the sample tubes under raised pressure. The nucleic acids absorbed onto the filter member through the step S1030 are not released with the washing solution, but the impurities are released from the filter member with the washing solution and removed from the samples.

Subsequently, the first and second racks 110 and 120 are driven to have an arrangement rotation, in step S1040. The step S1040 is to arrange the positions of the first and second racks 110 and 120 in order to perform an eluting operation. More specifically, the rotational drivers 140 and 140' rotate at least one of the first rack 110 or the second rack 120 so that the sample tubes 200 received into the first rack 110 are positioned on the elution tubes 300 of the second rack 120.

Finally, an eluting operation is carried out, in step S1050. The step S1050 is performed in such a manner that the first and second racks 110 and 120 are driven to have a synchronous rotation, thereby injecting an eluting solution into a plurality of the sample tubes 200 and maintaining the inside of the sample tubes under raised pressure. At this point, the eluting solution is used to release the nucleic acids absorbed on the filter member, and the released nucleic acids are received into the elution tubes 300.

According to the embodiment, at least either one of the step S1030 or the step S1050 may be performed multiple times, and a different washing solution or a different eluting solution may be used in each step.

Figure 11:
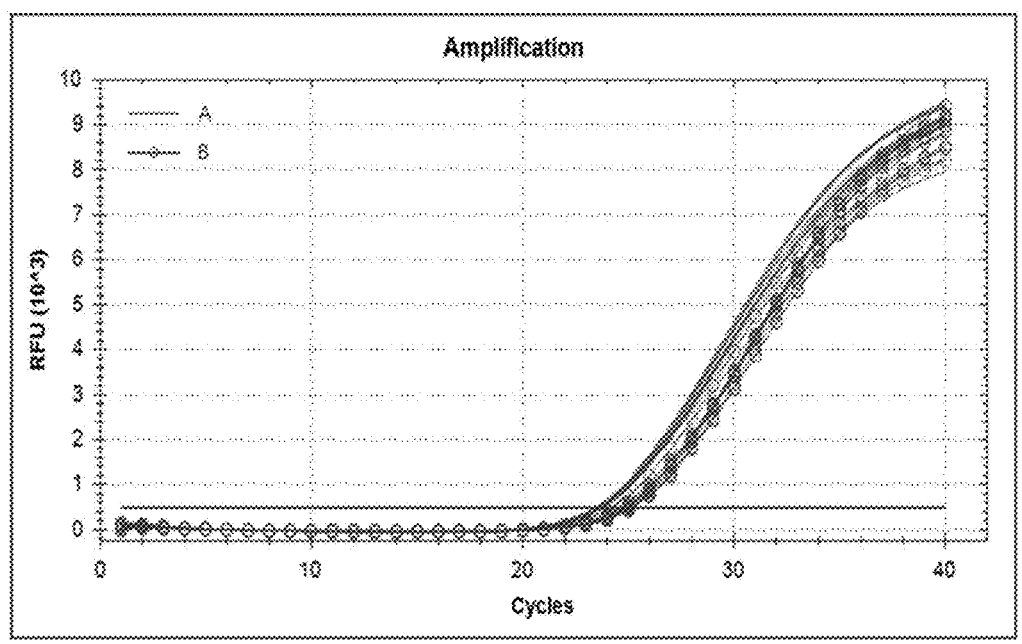
FIG. 11 shows an experimental example of the apparatus for nucleic acid extraction in accordance with one embodiment of the present invention.

FIG. 11 shows an experimental example of the apparatus for nucleic acid extraction in accordance with one embodiment of the present invention.

This experimental example involves the pre-treatment using a nucleic acid extraction apparatus A according to one embodiment of the present invention or a nucleic acid extraction apparatus B of the Q company and performs a PCR using the results of the pre-treatment.

The conditions and results of the experiment in the pre-treatment are given as follows.

TABLE 1

| Sample | Salnomella spp. Culture 1 × 10$^5$ CFU/ul 100 ul | |
|---|---|---|
| Lysis buffer volume | 500 ul (1:5) | |
| Lysis time/temp. | 5 min/room temperature | |
| Washing type | NBS washing buffer 1/600 ul | |
| (2 steps)/volume | NBS washing buffer 2/600 ul | |
| Elution buffer | NBS elution buffer | |
| Elution time | 1 min | |
| Running time | A | B |
| | Around 29 min/16 prep. | Around 60 min/12 prep. |
| | (around 4 min/1 prep.) | (around 60 min/1 prep.) |

As presented in the above table, the running time of the nucleic acid extraction apparatus A was shorter than that of the nucleic acid extraction apparatus B of the Q company by about 30 minutes in the 16 prep. Further, the nucleic acid extraction apparatus A had the higher speed in the pre-treatment on one sample.

The results of the pre-treatment were used to perform a PCR. The composition (Table 2) of the PCR reagent as used herein and the PCR conditions (Table 3) are given as follows.

TABLE 2

| Composition | Volume (ul) |
|---|---|
| 2x NBS master mix | 1x |
| Primer (F/R) | 1 uM |
| Probe | 0.5 uM |
| Template Vol. | 1 ul |
| Total | 20 ul |

TABLE 3

| PCR step | Temperature (° C.) | Time (sec.) | Cycle |
|---|---|---|---|
| Pre-Denaturation | 95 | 8 | 1 |
| Denaturation | 95 | 8 | 40 |
| Annealing | 68 | 14 | 40 |

Referring to FIG. 11, the PCR results of the nucleic acid extraction apparatus of the present invention according to the above conditions are presented. As illustrated, the nucleic acid extraction apparatus A offered higher PCR performance and higher efficiency of nucleic acid extraction than the nucleic acid extraction apparatus B of the Q company. Particularly, the nucleic acid extraction apparatus A was 1.5 time higher in the efficiency of the nucleic acid extraction than the nucleic acid extraction apparatus B in consideration of the fact that the Ct difference was 3.3 whenever the DNA increased 10 times in the real-time PCR.

The preferred embodiment of the present invention has been disclosed as above in the drawings and the specification of the present invention. Specific terms adopted in the specification of the present invention are used merely for the sake of the best explanation of the present invention and not to be confined to the common or dictionary meanings or construed to limit the scope of the present invention as defined in the claims of the invention. Therefore, it should be apparent to those skilled in the art that many equivalents and variations that may replace the embodiments given herein are possible in the light of the teaching of the present disclosure. Accordingly, the scope of the technical protection of the present invention should be defined by the technical conceptions of the claims of the present invention.

Though the order of the steps is specified in the drawings, it should not be construed that the steps are performed in a specified order or a sequential order so as to accomplish desired results or that all the specified steps are need to be performed. Under certain circumstances, multitasking or parallel processing may be advantageous.

What is claimed is:

1. An apparatus for nucleic acid extraction comprising:
a first rack having a plurality of sample tube receivers arranged in a circle;
a second rack having a plurality of elution tube receivers arranged in a circle and a washing solution receiver disposed at the center thereof, a part of the washing solution receiver extending outwards radially out from the center of the second rack to have a plurality of projections formed in alternation with the plurality of elution tube receivers;
a frame holding the first rack over the second rack;
a rotational driver rotating the first rack and the second rack, synchronously or separately;
a dispenser dispensing a washing solution and an eluting solution into the plurality of sample tubes, respectively; and
a pressurizer pressurizing the plurality of sample tubes, wherein the rotational driver has a configuration to rotate the first rack and the second rack to locate the plurality of sample tubes in the first rack to be lined up with the washing solution receiver or a plurality of elution tubes in the second rack, and a washing operation or an eluting operation is carried out when the first and second racks are driven to have a synchronous rotation.

2. The apparatus for nucleic acid extraction of claim 1, wherein the rotational driver is configured to adjust a location of the plurality of sample tube receivers to line up with the plurality of elution tube receivers or the plurality of projections.

3. The apparatus for nucleic acid extraction of claim 1, wherein at least one of the first rack and the second rack is detachably attached to the main body.

4. The apparatus for nucleic acid extraction of claim 1, further comprising:
a washing solution collector located under the washing solution receiver and shaped to receive a fluid from the washing solution receiver.

5. The apparatus for nucleic acid extraction of claim 4, wherein the washing solution collector is detachably attached to the second rack.

6. The apparatus for nucleic acid extraction of claim 1, wherein each of the plurality of sample tubes comprises:
a filter member absorbing nucleic acid molecules, and
a filter fixer fixing the filter member inside each of the plurality of sample tubes, and
wherein the apparatus for nucleic acid extraction further comprises a plurality of elution tubes accommodated in the plurality of elution tube receivers of the second rack.

7. The apparatus for nucleic acid extraction of claim 1, further comprising:
at least one washing solution container storing the washing solution; and
at least one eluting solution container storing the eluting solution.

8. The apparatus for nucleic acid extraction of claim 1, wherein the dispenser injects the washing solution into the plurality of sample tubes when the first rack and the second rack have the synchronous rotation after the rotational driver rotates the first rack and the second rack to locate the plurality of sample tubes in the first rack to be lined up with the washing solution receiver.

9. The apparatus for nucleic acid extraction of claim 1, wherein the dispenser injects the eluting solution into the plurality of sample tubes when the first rack and the second rack have the synchronous rotation after the rotational driver rotates the first rack and the second rack to locate the plurality of sample tubes in the first rack to be lined up with the plurality of elution tubes in the second rack.

10. The apparatus for nucleic acid extraction of claim 1, wherein each of the plurality of sample tubes includes a filter support having a projection with a tapered cross-sectional area in a longitudinal direction and disposed inside bottom of each of the plurality of sample tubes.

11. The apparatus for nucleic acid extraction of claim 1, wherein one end of each of the plurality of sample tubes is faced to the plurality of projections at the washing solution receiver.

12. The apparatus for nucleic acid extraction of claim 1, wherein at least one of the first rack or the second rack is movable in a horizontal direction with respect to the main body.

13. An operation method for the nucleic acid extraction apparatus of claim 1, the operation method comprising:

rotating at least one of the first rack and the second rack so that the plurality of sample tubes in the first rack corresponds to the washing solution receiver of the second rack, wherein
the plurality of sample tubes receive a sample solution containing nucleic acids and impurities, the nucleic acids being absorbed onto a filter member in each of the plurality of sample tubes;
performing the washing operation for releasing the impurities from the filter member while rotating the first rack and the second rack to have the synchronous rotation;
rotating at least one of the first rack and the second rack so that the plurality of sample tubes in the first rack corresponds to the plurality of elution tubes in the second rack; and
performing the eluting operation for releasing the nucleic acids absorbed on the filter member while rotating the first rack and the second rack to have the synchronous rotation.

14. The operation method of claim 13, wherein the performing the washing operation comprises driving the synchronous rotation of the first and second racks to inject a washing solution into the plurality of sample tubes and pressurizing the plurality of sample tubes, wherein the washing solution releases the impurities from the filter member.

15. The operation method of claim 13, wherein the performing the eluting operation comprises driving the synchronous rotation of the first and second racks to inject an eluting solution into the plurality of sample tubes and pressurizing the plurality of sample tubes, wherein the eluting solution releases the nucleic acids absorbed onto the filter member into the plurality of elution tubes.

16. The operation method of claim 13, wherein at least one of the washing operation or the eluting operation is performed repeatedly.

17. An apparatus for nucleic acid extraction comprising:
a first rack having a plurality of sample tube receivers arranged in a circle;
a second rack located under the first rack and having a plurality of elution tube receivers arranged in a circle and corresponding to the plurality of sample tube receivers, wherein the second rack has a washing solution receiver therein to receive a fluid, wherein the washing solution receiver is extended outwards radially from the center of the second rack to have a plurality of projections formed in alternation with the plurality of elution tube receivers;
a rotational driver rotating the first rack and the second rack, synchronously or separately;
a dispenser dispensing a washing solution and an eluting solution into the plurality of sample tubes, respectively; and
a pressurizer pressurizing the plurality of sample tubes,
wherein the rotational driver has a configuration to rotate the first rack and the second rack to locate the plurality of sample tubes in the first rack to be lined up with the washing solution receiver or a plurality of elution tubes in the second rack, and
a washing operation or an eluting operation is carried out when the first and second racks are driven to have a synchronous rotation.

18. The apparatus for nucleic acid extraction of claim 17, wherein the rotational driver is configured to adjust a location of the plurality of sample tube receivers to line up with the plurality of elution tube receivers or the plurality of projections.

19. The apparatus for nucleic acid extraction of claim 17, wherein the rotational driver includes a first rotational driver and a second rotational driver, wherein the first rotational driver rotates the first racks and the second rotational driver rotates the second rack, and wherein the first rotational driver rotates the first rack in a synchronous rotation movement with the second rack.

* * * * *